| (12) | United States Patent | (10) Patent No.: | US 7,718,399 B2 |
|---|---|---|---|
| | Jung et al. | (45) Date of Patent: | May 18, 2010 |

(54) **EXPRESSION VECTOR FOR SECRETING ANTIBODY FRAGMENT USING *E. COLI* SIGNAL SEQUENCE AND METHOD FOR MASS-PRODUCING ANTIBODY FRAGMENT**

(75) Inventors: Sung Youb Jung, Yongin-si (KR); Jin Sun Kim, Kwangmyung-si (KR); Se Chang Kwon, Seoul (KR); Gwan Sun Lee, Seoul (KR)

(73) Assignee: Hanmi Pharm. Co., Ltd, Kyungki-do (KR)

( * ) Notice: Subject to any disclaimer, the term of this patent is extended or adjusted under 35 U.S.C. 154(b) by 1069 days.

(21) Appl. No.: 10/576,068

(22) PCT Filed: Oct. 14, 2004

(86) PCT No.: PCT/KR2004/002625

§ 371 (c)(1),
(2), (4) Date: Apr. 14, 2006

(87) PCT Pub. No.: WO2005/038031

PCT Pub. Date: Apr. 28, 2005

(65) Prior Publication Data

US 2009/0104660 A1    Apr. 23, 2009

(30) Foreign Application Priority Data

Oct. 16, 2003   (KR) ..................... 10-2003-0072216

(51) Int. Cl.
  *C12P 21/06*   (2006.01)
  *C07K 14/00*   (2006.01)
(52) U.S. Cl. .................. 435/69.1; 435/320.1; 530/350; 530/351
(58) Field of Classification Search ....................... None
  See application file for complete search history.

(56) References Cited

U.S. PATENT DOCUMENTS 5,648,237 A    7/1997   Carter

OTHER PUBLICATIONS

D.P. Humphreys et al., "A plasmid system for optimization of Fab production in *Escherichia coli*: importance of balance of heavy chain and light chain systhesis", In: Protein Expr. Purif., Nov. 2002, vol. 26(2), pp. 309-320.

J.F. Rippmann et al., "Procaryotic expression of single-chain variable-fragment (scFv) antibodies: Secretion in L-form cells of Proteus mirabilis leads to active product and overcomes the limitations of periplasmic expression in *Escherichia coli*", In: Appln Environ. Microbiol., Dec. 1998, vol. 64(12), pp. 4862-4869.

*Primary Examiner*—Karen Cochrane Carlson
(74) *Attorney, Agent, or Firm*—Sughrue Mion, PLLC

(57) ABSTRACT

A recombinant expression vector capable of expressing and secreting an antibody fragment fused with *E. coli* thermostable enterotoxin signal sequence derivative or *E. coli* outer membrane protein A (Omp A) signal sequence in the form of a soluble heterozygote protein is used to mass-produce the antibody fragment by culturing a microorganism transformed with the expression vector in a medium and collecting the antibody fragment secreted from the transformed microorganism into the medium.

19 Claims, 9 Drawing Sheets

EXPRESSION VECTOR FOR SECRETING ANTIBODY FRAGMENT USING E. COLI SIGNAL SEQUENCE AND METHOD FOR MASS-PRODUCING ANTIBODY FRAGMENT

This is a National Stage application under 35 U.S.C. §371 of PCT/KR2004/002625 filed on Oct. 14, 2004, which claims priority from Oct. 16, 2003, all of which are incorporated herein by reference.

FIELD OF THE INVENTION

The present invention relates to a recombinant expression vector secretively expressing an antibody fragment fused with an *E. coli* signal sequence in the form of a soluble heterozygote; a microorganism transformed with the expression vector; and a method for mass-producing the antibody fragment using the transformed microorganism.

BACKGROUND OF THE INVENTION

An "antibody fragment", as used herein, shall mean the portion of an antibody comprising an antigen-binding region or a variable region thereof. Exemplary antibody fragments are Fab, Fab', $F(ab')_2$ and scFv fragments. Papain digestion of antibodies produces two identical antigen-binding fragments, called Fab fragments, each with a single antigen-binding site, and a residual Fc fragment. When an antibody is treated with pepsine, $F(ab')_2$ fragment having two antigen-binding sites which is still capable of forming a cross-linking is produced. The Fab fragment also contains a constant domain of the light chain and a first constant domain (CH1) of the heavy chain. Fab' fragments differ from Fab fragments by the addition of a few residues at the carboxy terminus of the heavy chain CH1 domain including one or more cysteines from a hinge region of the antibody.

In order to modify the inherent properties of an antibody by increasing the antibody binding affinity, changing the antigenicity or preparing a double specific antibody, various methods for the production of antibodies and fragments thereof using a gene recombinant technique have been studied. As a result, a method for producing an antibody and fragments thereof using an *E. coli* expression system has been developed. The production method using an *E. coli* expression system has several advantages over other conventional methods based on an animal cell expression system: 1) since it is easy to construct an expression vector, the expression thereof can be easily checked; 2) it is possible to mass-produce an antibody at a low cost because of the fast growth rate of *E. coli*, which facilitates securing antibody samples for experimental studies; and 3) application of the relatively simple fermentation method may allow an easier commercialization than those methods employing other host cells.

There have been several reports that an antibody-encoding gene is introduced into *E. coli* and expressed therein (Cabilly et al., *Proc. Natl. Acad. Sci. USA* 81: 3273-3277, 1984; and Boss et al., *Nucleic Acids Res.* 12: 3791-3806, 1984). These reports have disclosed that antibody molecules are expressed at various yields in a cytoplasmic space, and also that *E. coli* can be used as a host cell for secretively expressing an immunoglobulin light chain (Zemel-Dreasen et al., *Gene* 315-322, 1984), or for secreting an antibody fragment fused with alkaline phosphatase or β-lactamase signal sequence into a periplasmic space (Pluckthun et al., *Cold Spring Harbor Symposiua on Quantitative Biology* Volume LII, 105-112, 1987). International Patent Publication No. WO 92/01059 teaches that the Fab'-encoding gene which recognizes a specific site of a cancer cell is expressed in the form of a fusion protein with *E. coli* outer membrane protein A (OmpA) signal sequence; and U.S. Pat. No. 5,648,237 discloses that the Fab'-encoding gene fused with *E. coli* enterotoxin signal sequence is expressed under the control of PhoA promoter.

An expressed antibody fragment shows an antigen-binding affinity similar to a wild-type antibody; however, since it is smaller than the wild-type, its local invasiveness is higher (Blumenthal et al., *Adv. Drug Del. Rev.* 4: 279, 1990), and as it does not contain any Fc region, no side-effect is induced when administered to a human body. Accordingly, an antibody fragment may be used to prepare a diagnostic reagent or to develop a therapeutic antibody, and the mass-production thereof in *E. coli* becomes economically attractive. In case of preparing an antibody fragment from a wild-type antibody, the wild-type antibody must be digested with a proteinase and purified, which is cumbersome and economically unfavorable.

However, there are several problems associated with the production of an antibody fragment in *E. coli*. First, not all antibody fragments can be expressed in an amount sufficient for intended therapeutic or diagnostic purpose, and sometimes the cultivation procedure must be repeated several times. Further, to endow the antibody fragment with functional activity, both the heavy chain and the light chain have to be expressed in a single cell and maintain a heterozygote form via a disulfide bond formed between them, which requires that the antibody fragment must be expressed in a highly soluble form, and not in the form of an inclusion body which is frequently found when a protein is overly expressed in *E. coli*. To solve such problems, a method for secreting an expressed antibody fragment into a periplasmic space using a signal sequence has been actively studied. However, it has been reported that not all antibody fragments fused with the signal sequence are secretively over-expressed into the periplasmic space of *E. coli*, and the amount of the expressed antibody varies greatly with the nucleotide sequence thereof (Kelly et, al., *Biochemistry* 31: 5434-5441, 1992; and Humphreys et, al., *Protein Expression and Purification* 26: 309-320, 2002). It has also been found that the expression pattern of an antibody fragment fluctuates depending on the difference in the expression vector's structural gene or the distance between the genes encoding the heavy chain and the light chain (International Patent Publication No: WO 01/94585). These facts suggest that for the expression of a target antibody fragment, a proper balance must be maintained in terms of the interaction between the target antibody gene and the host structural gene essential for the expression and the interaction between the target and signal sequences in case signal sequences are used.

The present inventors have therefore endeavored to develop a method for expressing in *E. coli* an antibody fragment in a soluble heterolzygote form having a desired antigen-binding affinity by preparing a recombinant expression vector which secretively expresses human antibody Fab' of tumor necrosis factor-alpha (TNF-α) as a target antibody fragment using *E. coli* thermostable enterotoxin signal sequence or *E. coli* outer membrane protein A (Omp A) signal sequence.

SUMMARY OF THE INVENTION

Accordingly, an object of the present invention is to provide a recombinant expression vector which is capable of over-expressing an antibody fragment having an antigen-binding affinity in a soluble heterozygote form using an *E. coli* signal sequence and a microorganism transformed with the expression vector.

Another object of the present invention is to provide a method for producing the antibody fragment using the transformed microorganism.

In accordance with one aspect of the present invention, there is provided a recombinant expression vector comprising a gene encoding a light chain of an antibody fragment fused with a first *E. coli* signal sequence and a gene encoding a heavy chain of the antibody fragment fused with a second *E. coli* signal sequence, wherein the antibody fragment expressed from the expression vector is secreted into a culture medium.

In accordance with another aspect of the present invention, there is provided a method for producing the antibody fragment which comprises the steps of: preparing the above expression vector; transforming a microorganism with the expression vector; culturing the microorganism in a medium; and collecting the antibody fragment secreted from the microorganism into the medium.

BRIEF DESCRIPTION OF THE DRAWINGS

The above and other objects and features of the present invention will become apparent from the following description of the invention, when taken in conjunction with the accompanying drawings which respectively show.

DETAILED DESCRIPTION OF THE INVENTION

Figure 1:
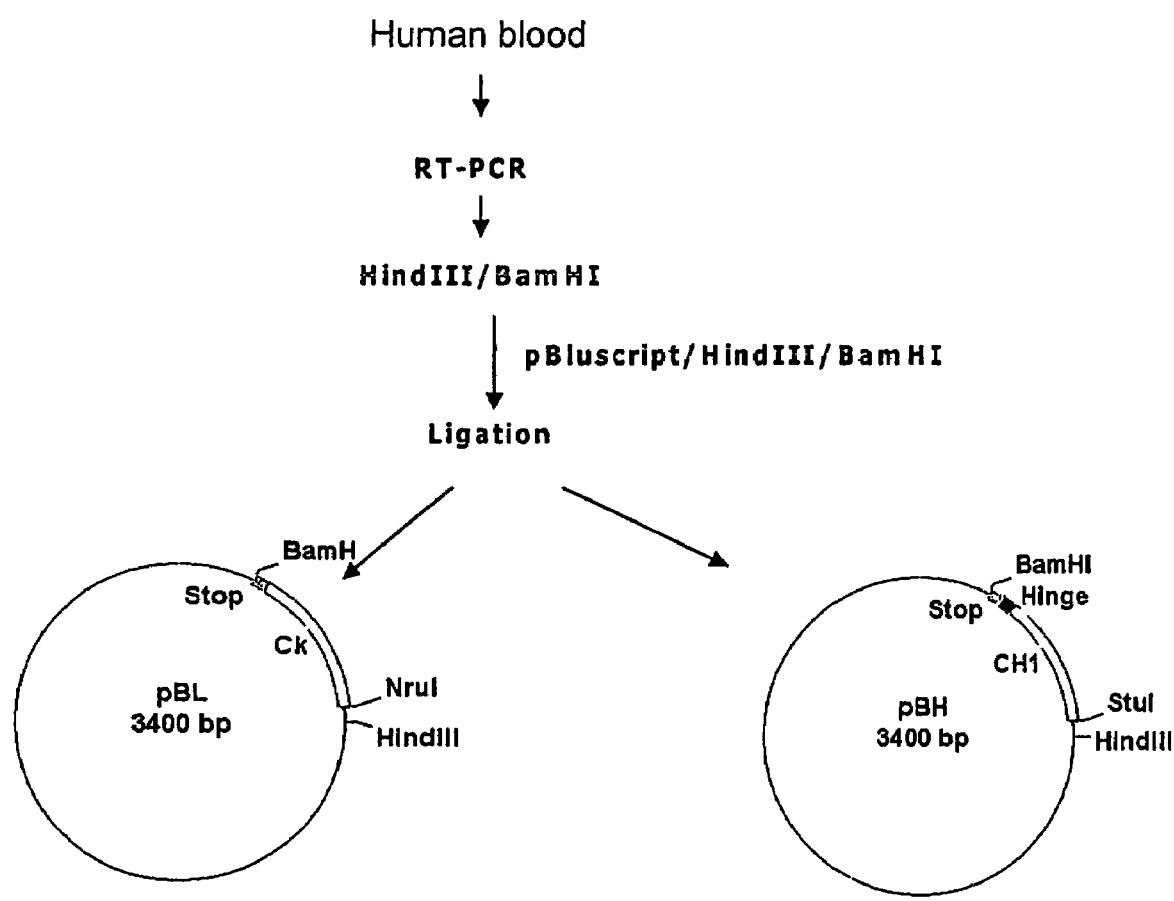
FIG. 1: the procedures of constructing plasmids pBH and pBL by inserting constant regions of the heavy chain and the light chain into plasmid pBluescript SK(-), respectively.

The present invention provides a recombinant expression vector comprising a gene encoding a light chain of an antibody fragment fused with a first *E. coli* signal sequence and a gene encoding a heavy chain of the antibody fragment fused with a second *E. coli* signal sequence, wherein the antibody fragment expressed from the expression vector is secreted into a culture medium; and a microorganism transformed with the expression vector.

The expression vector which is capable of secretively expressing the antibody fragment, functionally similar to a wild-type antibody, is prepared by fusing each of the genes encoding the light chain and the heavy chain of a human antibody with *E. coli* thermostable enterotoxin signal sequence derivative or *E. coli* outer membrane protein A (OmpA) signal sequence.

The antibody fragment of the present invention may be Fab, Fab', F(ab')$_2$ or scFv fragment, preferably Fab'. The Fab fragment contains a constant domain of the light chain and a first constant domain (CH1) of the heavy chain. Fab' fragments differ from Fab fragments by the addition of a few residues at the carboxy terminus of the heavy chain CH1 domain including one or more cysteines from a hinge region of the antibody. Further, the F(ab')$_2$ fragment is made by linking two Fab' molecules with a disulfide bond, and the scFv fragment exists as a single polypeptide chain formed by coupling only variable regions of the light chain and the heavy chain with a peptide linker.

The antibody fragment employable in the present invention includes all antibodies capable of selectively binding to an antigen, wherein the antigen may be an antigen bound to a cell surface such as T cell, endothelial cell, or a cancer cell marker, or a free soluble antigen which does not bind to a cell. The antigens bound to a cell surface may include, but are not limited to, β1 integrins, P-selectin, E-selectin, CD2, CD3, CD4, CD5, CD7, CD8, CD11a, CD11b, CD18, CD19, CD20, CD23, CD25, CD33, CD38, CD40, CD45, CD69, MHC class I, MHC class II, VEGF and other receptors. Further, the soluble antigens may include, but are not limited to, interleukins such as IL-1, 2, 3, 4, 5, 6, 8 and IL-12; virus antigen such as cytomegalovirus antigen; immunoglobulin such as IgE; interferon such as IFN-α, β and γ; factors relating to cell growth and proliferation such as tumor necrosis factor-α and β, and platelet derived growth factor-α and β. In a preferred embodiment, the present invention employs genes encoding the light chain and the heavy chain of the antibody fragment of anti-tumor necrosis factor-α (TNF-α). It has been known that TNF-α induces the syntheses of IL-1, IL-6 and IL-8 that are known as cytokines generated by immune-relating cells such as monocytes or macrophages and causes inflammation when over-expressed, and stimulates the secretion of the proteinase which destroys the cartilage tissue, thus acting as a key mediator causing arthritis. The Fab' of anti-tumor necrosis factor-α as an arthritis therapeutics has to be derived from a monoclonal antibody, preferably a humanized antibody, more preferably a complete human antibody.

There have been already reported genes encoding complementary determining regions (CDR) of several chimeric antibodies or humanized antibodies of anti-tumor necrosis factor-α, and the nucleotide sequence of a complete human antibody gene has been determined (International Patent No: WO 97/29131). Accordingly, it is possible to artificially synthesize a gene encoding the antibody fragment based on such information using a nucleotide synthesizer and clone the synthesized genes encoding the heavy chain and the light chain of Fab through a series of annealing and ligation procedures, or ligation-chain reaction (LCR) and polymerase chain reaction (PCR).

In a preferred embodiment, the present invention prepares the light chain and the heavy chain variable regions by synthesizing the gene fragments encoding the light chain variable region of human anti-tumor necrosis factor-α Fab' having the nucleotide sequences of SEQ ID NOs: 1 to 6 and the gene fragments encoding the heavy chain variable region having the nucleotide sequences of SEQ ID NOs: 7 to 12 using a nucleotide synthesizer, and linking these synthesized fragments together via PCR. Further, the gene fragment comprising the light chain constant region and the heavy chain constant region including CH1 and hinge region of IgG1 is prepared by RT-PCR using a total RNA extracted from human blood as a template and a pair of primers specific for the light chain and the heavy chain constant regions of human anti-tumor necrosis factor-α Fab'. Each of the prepared gene fragments encoding the light chain and the heavy chain constant regions is cloned into a proper expression vector, to prepare plasmid pBLC comprising the gene encoding the constant region of the light chain as well as plasmid pBHC comprising the gene encoding the constant region of the heavy chain (see FIGS. 1 and 2). As a result of the nucleotide sequencing analysis, it has been found that the gene encoding the constant region of the light chain inserted into plasmid pBLC has the nucleotide sequence of SEQ ID NO: 32, and the gene encoding the constant region of the heavy chain inserted into plasmid pBHC has the nucleotide sequence of SEQ ID NO: 33.

The antibody fragment to be expressed may exist as a heterozygote having two different proteins consisting of the heavy chain and the light chain. Accordingly, in order to prepare the antibody fragment as an active heterozygote having antigen-binding affinity, the heavy chain and the light chain must be simultaneously expressed at a similar level and a disulfide bond has to be formed at an accurate site between the heavy chain and the light chain expressed from the expression vector. Further, when the antibody fragment is expressed in *E. coli*, the protein expressed in a cytoplasm may exist in the form of an inclusion body. In this case, it happens that the disulfide bond between the heavy chain and the light chain may not be formed at an accurate site, and even if expressed in a soluble form, it may be difficult to completely destroy the cells during the purification step. To solve these problems, the present invention provides a recombinant expression vector secreting the antibody fragment expressed from the vector into a periplasmic space of *E. coli* or into the culture medium using an *E. coli* signal sequence.

When the expressed protein exists in the culture medium, there is no need to carry out the cumbersome process of destroying the cells, as is required when the expressed protein exists within bacterial cells. In addition, since the expressed protein exists at the periplasmic space, it can be harvested without going through such procedure as osmotic shock treatment after collecting cells. Further, as an oxidative environment facilitates the formation of a disulfide bond to give a heterozygote, it is advantageous that the expressed protein exists in the periplasmic space or the culture medium rather than in the non-oxidative environment of cell's cytoplasm.

The *E. coli* signal sequences employable in the inventive recombinant expression vector may include, but are not limited to, *E. coli* thermostable enterotoxin signal sequence, OmpA signal sequence, β-lactamase signal sequence, Gene III signal sequence and PelB signal sequence or a derivative thereof, preferably *E. coli* thermostable enterotoxin signal sequence derivative or OmpA signal sequence.

In a preferred embodiment of the present invention, the *E. coli* thermostable enterotoxin signal sequence derivative used for secreting the active antibody fragment Fab' expressed from the expression vector into a culture medium has been developed by the present inventors to express several foreign proteins in *E. coli*. It has been found that the *E. coli* thermostable enterotoxin signal sequence derivative has the nucleotide sequence of SEQ ID NO: 17 and is capable of expressing and secreting various foreign proteins in *E. coli* at an optimum efficiency (Korean Patent No: 316347). In the present invention, a recombinant expression vector which can secrete an active form of Fab' expressed from the expression vector into a culture medium is prepared by fusing each of the genes encoding the heavy chain and the light chain of an antibody fragment with the *E. coli* signal sequence, e.g., *E. coli* thermostable enterotoxin signal sequence derivative or outer membrane protein A signal sequence.

In order to express the genes encoding the heavy chain and the light chain of an antibody fragment in one expression vector, the present invention provides two kinds of expression vectors: the expression vector using a di-cistronic system which can simultaneously express two proteins by arranging the genes at proper intervals under a single promoter, and the other expression vector using a dual-promoter system which can independently express two proteins by coupling the genes to the respective promoters.

First, a gene fragment encoding human growth hormone (hGH) is removed from expression vector pT14S1SH-4T20V22Q (Korean Patent No: 316347) which comprises the *E. coli* thermostable enterotoxin signal sequence derivative and hGH gene. The gene fragment encoding the light chain obtained from plasmid pBLC and the gene fragment encoding the heavy chain obtained from plasmid pBHC are inserted into the expression vector pT14S1SH-4T20V22Q, to obtain expression vector pmsHC comprising the gene fragment encoding the heavy chain fused with the thermostable enterotoxin signal sequence derivative, and expression vector pmsLC comprising the gene fragment encoding the light chain fused with the thermostable enterotoxin signal sequence derivative. In order to construct a di-cistronic expression vector so that each of the genes encoding the heavy chain and the light chain is fused with the *E, coli* thermostable enterotoxin secretion sequence derivative, and a single promoter regulates the expression of the genes encoding the light chain and the heavy chain, the gene fragment encoding the heavy chain obtained from the plasmid pmsHC by PCR is inserted into the plasmid pmsLC, to obtain expression vectors psDLHF_B and psDLHF_Bp (see FIGS. 3 and 4).

Figure 5:
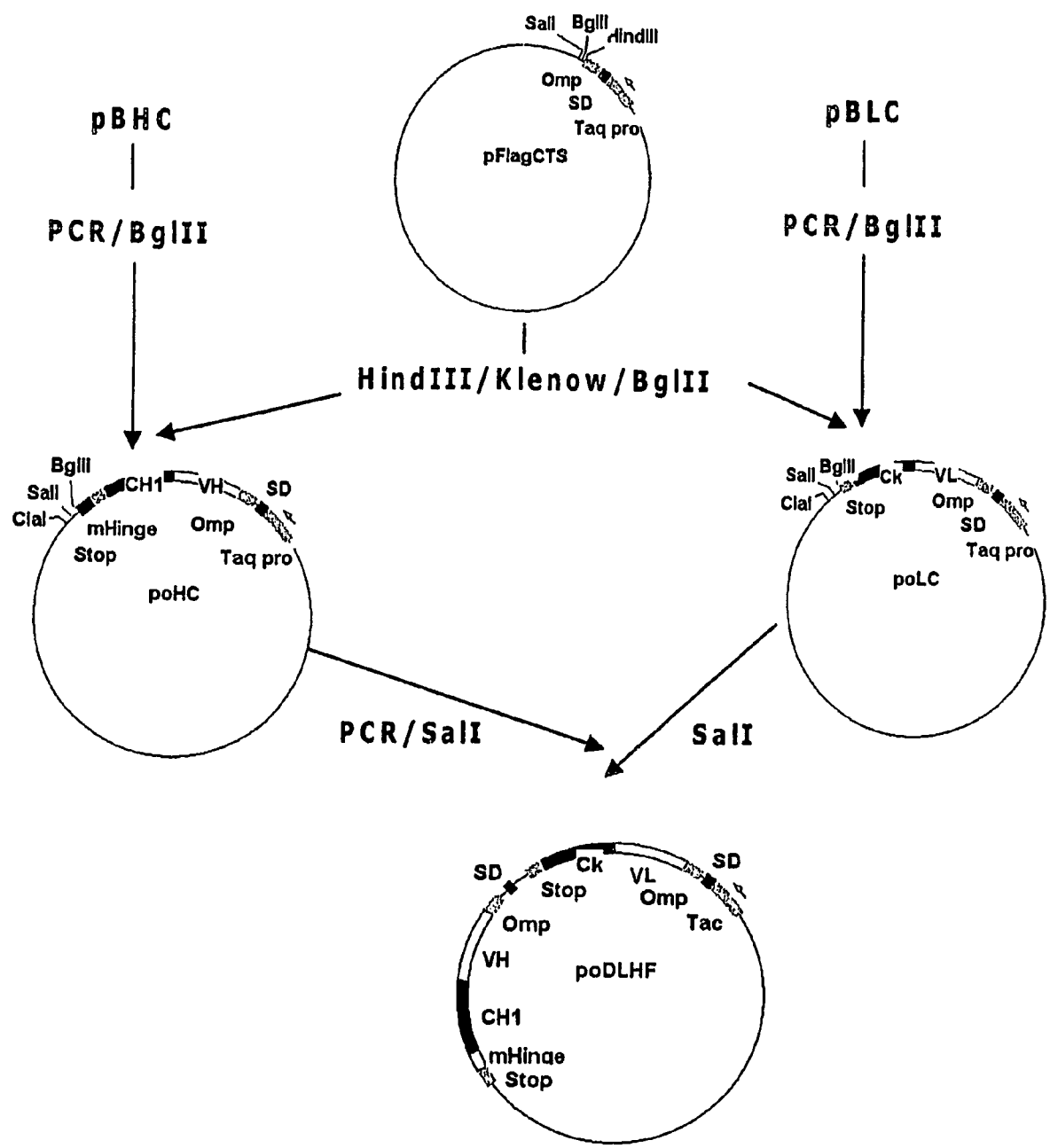
FIG. 5: the procedure of constructing expression vector poDLHF comprising Tac promoter and genes encoding the light chain and the heavy chain of the antibody fused with *E. coli* outer membrane protein A (OmpA) signal sequence.

Further, the present invention has constructed expression vector poDLHF that each of the genes encoding the light chain and the heavy chain is fused with the *E. coli* OmpA signal sequence (SEQ ID NO: 24) and a single Tac promoter regulates the expression of the genes encoding the light chain and the heavy chain (see FIG. 5), by the same method described above.

The expression vectors psDLHF_B, psDLHF_Bp and poDLHF thus prepared are bi-cistronic expression vectors: each of the heavy chain and the light chain of anti-tumor necrosis factor-α Fab' fused with the signal sequence is expressed and secreted under the control of a single promoter.

*E. coli* transformants BL21(DE3)/psDLHF_B(HM10920), BL21 (DE3)/psDLHF_BP(HM10921) and BL21/poDLHF (HM10922) prepared by transforming each of the above expression vectors into *E. coli* BL21(DE3) have been deposited at Korean Culture Center of Microorganism on Oct. 2, 2003 under the accession numbers of KCCM-10509, KCCM-10510 and KCCM-10511, respectively, in accordance with the terms of the Budapest Treaty on the International Recognition of the Deposit of Microorganisms for the Purposes of Patent Procedure.

Figure 6:
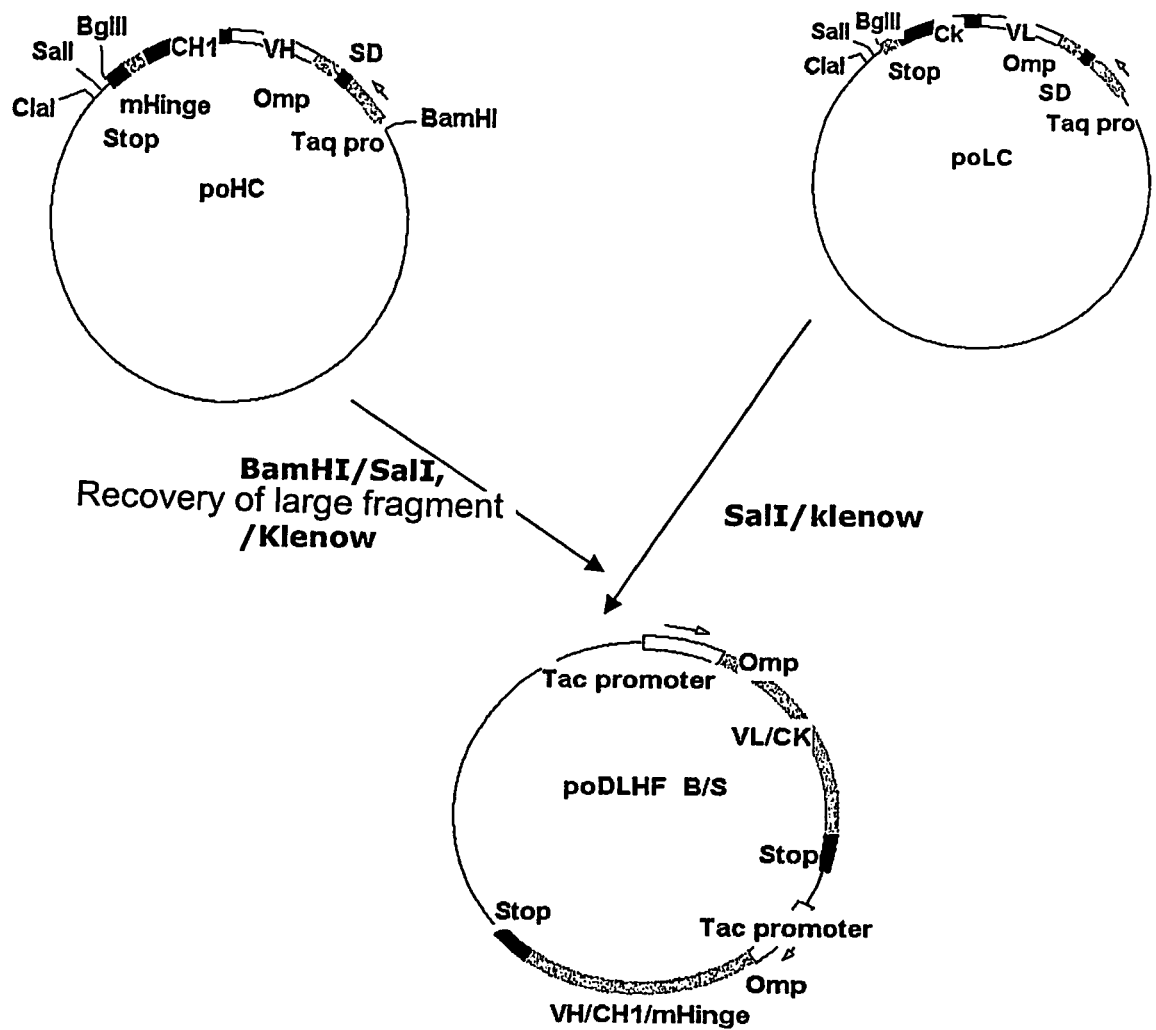
FIG. 6: the procedure of constructing expression vector poDLHF_B/S that expresses and secretes the heavy chain and the light chain under the control of distinct Tac promoters.

In case of secretively expressing two different proteins under the control of a single promoter, as mentioned above, the expression efficiency of the gene closer to the promoter may be differed from that of the gene farther away (Humphreys et, al., *Protein Expression and Purification* 26: 309-320, 2002). Therefore, the present invention provides an expression vector which uses a dual-promoter system so that the expression and secretion of the heavy chain and the light chain of anti-tumor necrosis factor-α Fab' can be independently regulated by distinct promoters. In a preferred embodiment, the present invention has prepared expression vector poDLHF_B/S that each of the genes encoding the heavy and light chain of anti-tumor necrosis factor-α Fab' is fused with the OmpA signal sequence and the respective Tac promoters regulate the expression of the genes encoding the light chain and the heavy chain (see FIG. 6). *E. coli* transformant BL21/poDLHF_B/S(HM10923) prepared by transforming the expression vector poDLHF_B/S into *E. coli* BL21 has been deposited at Korean Culture Center of Microorganism on Oct. 2, 2003 under the accession number of KCCM-10512, in accordance with the terms of the Budapest Treaty on the International Recognition of the Deposit of Microorganisms for the Purposes of Patent Procedure.

The formation of a heterozygote such as an antibody fragment is inhibited when one of the two fragments of the heterozygote is over-expressed, and accordingly, the two protein fragments must be expressed at similar levels. Thus, the present invention provides a recombinant expression vector which can secretively express an antibody fragment by fusing each of the genes encoding the heavy chain and the light chain with respectively different signal sequences.

Figure 7:
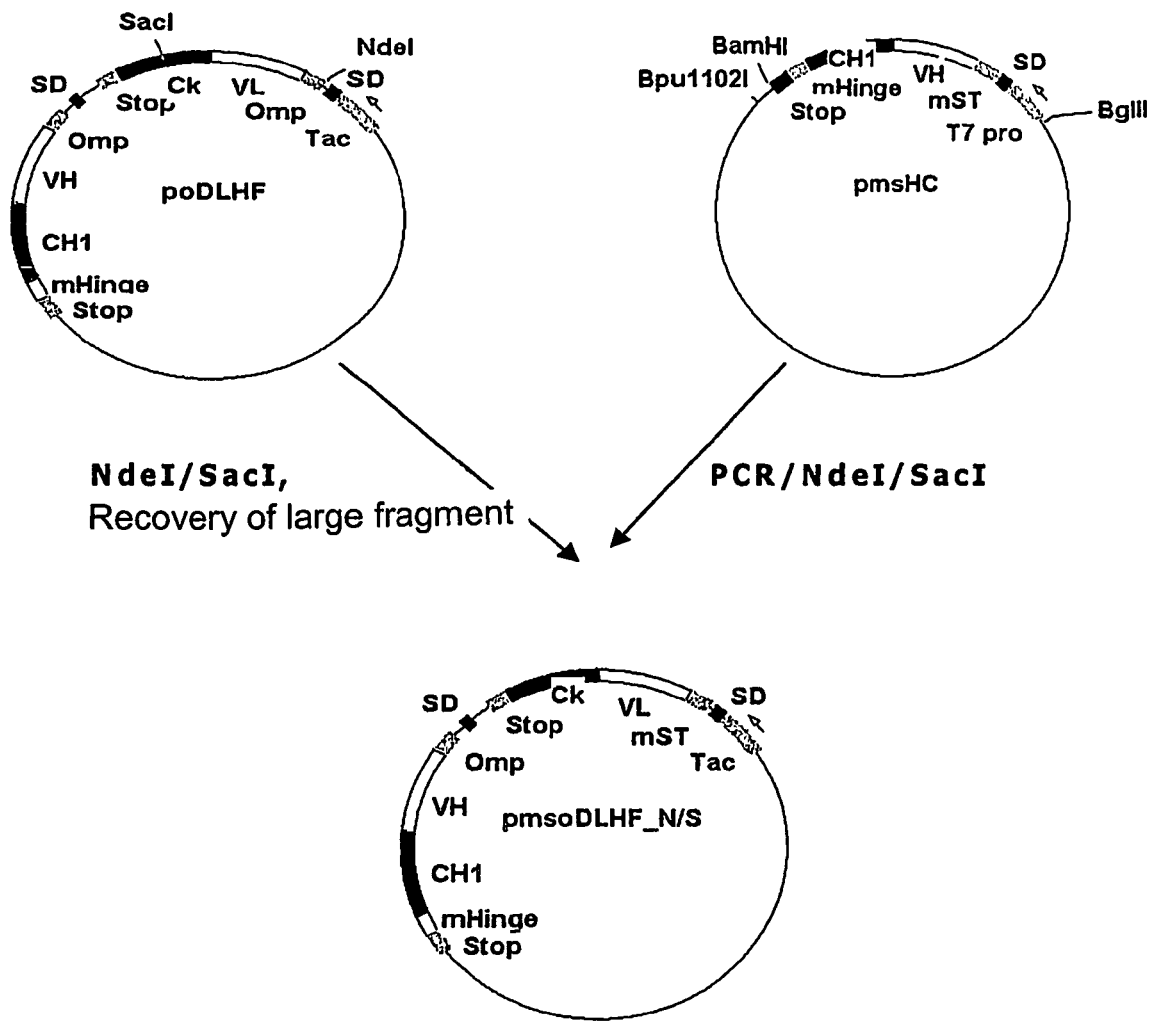
FIG. 7: the procedure of constructing expression vector pmsoDLHF_N/S in which a gene encoding the light chain of the antibody is fused with *E. coli* thermostable enterotoxin signal sequence and a gene encoding the heavy chain of the antibody is fused with *E. coli* outer membrane protein A (OmpA) signal sequence, the expression and secretion thereof being regulated by a single Tac promoter.
Figure 8:
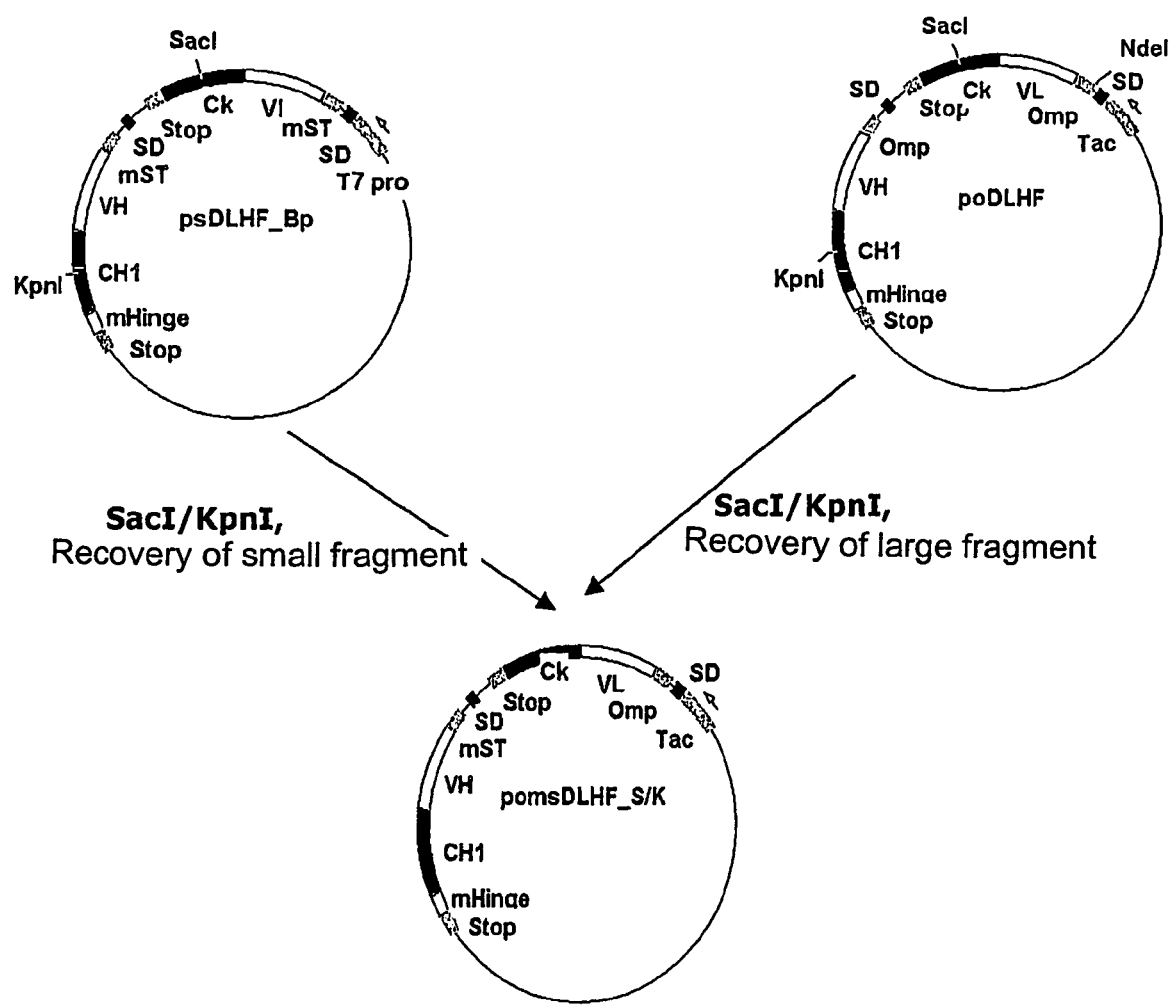
FIG. 8: the procedure of constructing expression vector pmsoDLHF_S/K in which a gene encoding the light chain of the antibody is fused with *E. coli* outer membrane protein A (OmpA) signal sequence and a gene encoding the heavy chain of the antibody is fused with *E. coli* thermostable enterotoxin signal sequence, the expression and secretion thereof being regulated by a single Tac promoter.

In a preferred embodiment of the present invention, expression vector pmsoDLHF_N/S is constructed such that the gene encoding the light chain of anti-tumor necrosis factor-α Fab' is fused with the thermostable enterotoxin signal sequence derivative, the gene encoding the heavy chain thereof is fused with the OmpA signal sequence, and a single T7 promoter regulates the expression of the genes encoding the light and heavy chain (see FIG. 7). Further, in the present invention, expression vector pmsoDLHF_S/K is constructed such that the gene encoding the heavy chain is fused to the thermostable enterotoxin signal sequence derivative, the gene encoding the light chain is fused with the OmpA signal sequence, and a single Tac promoter regulates the expression of the genes encoding the light chain and the heavy chain (see FIG. 8). *E. coli* transformants BL21/pmsoDLHF_N/S(HM10924) and BL21/pmsoDLHF_S/K(HM10925) prepared by introducing each of expression vectors pmsoDLHF_N/S and pmsoDLHF_S/K into *E. coli* BL21 have been deposited at Korean Culture Center of Microorganism on Oct. 2, 2003 under the accession numbers of KCCM-10513 and KCCM-10516, in accordance with the terms of the Budapest Treaty on the International Recognition of the Deposit of Microorganisms for the Purposes of Patent Procedure.

The present invention provides a recombinant microorganism prepared by introducing the inventive recombinant expression vector thus constructed into a proper host cell. Host cells employable in the present invention may include, but are not limited to, *E. coli* W3110, RV308, BL21, BL21 (DE3) and so on, preferably *E. coli* BL21. In case of culturing the recombinant microorganism transformed with the expression vector at a high concentration using a fermentor ($OD_{600}$=120 to 150), it has been found that the antibody fragment of anti-tumor necrosis factor-α is secretively produced in the culture medium at a high yield of over 100 to 500 mg per 1 l of culture medium (see Table 1). The antibody fragment of anti-tumor necrosis factor-α thus mass-produced can be partially purified with a protein-G affinity column. Reducing and non-reducing SDS-PAGE analyses of the purified antibody fragment of anti-tumor necrosis factor-α have shown that the antibody fragment is produced in the form of a soluble heterozygote (see FIG. 9). Further, ELISA analysis using anti-tumor necrosis factor-α as a binding antigen has revealed that the antibody fragment of tumor necrosis factor-α has good binding affinity to the tumor necrosis factor-α antigen (see FIG. 10).

The present invention further provides a method for producing an antibody fragment, comprising the steps of: preparing an expression vector comprising a gene encoding a light chain of the antibody fragment fused with a first *E. coli* signal sequence and a gene encoding a heavy chain of the antibody fragment fused with a second *E. coli* signal sequence; transforming a microorganism with the expression vector; culturing the microorganism in a medium; and collecting the antibody fragment secreted from the microorganism into the medium.

The *E. coli* signal sequences employable in the inventive recombinant expression vector may include, but are not limited to, *E. coli* thermostable enterotoxin signal sequence, OmpA signal sequence, β-lactamase signal sequence, Gene III signal sequence and PelB signal sequence or a derivative thereof, preferably *E. coli* thermostable enterotoxin signal sequence derivative having the nucleotide sequence of SEQ ID NO: 17 or OmpA signal sequence having the nucleotide sequence of SEQ ID NO: 23.

After the microorganism transformed with the recombinant expression vector is pre-cultured in a proper medium, the pre-culture solution is inoculated into a fermentor and subjected to main-culture under an aerobic condition at a temperature ranging from 30 to 35° C. When the OD value at 600 nm reaches 80, an inducer is added to the fermentor to induce the expression of the target antibody fragment. Preferably, the inducer employable in the present invention is, but not limited to, IPTG. The cultivation is further carried out for 40 to 45 hrs until the OD value at 600 nm reaches the range of 120 to 140. After the culture solution is subjected to centrifugation to separate a supernatant, the supernatant is subjected to affinity column chromatography to purify the antibody fragment. Preferably, the transformant microorganisms may include, but are not limited to, *E. coli* BL21(DE3)/psDLHF_B (HM10920) (KCCM-10509), BL21 (DE3)/psDLHF_BP (HM10921) (KCCM-10510), BL21/poDLHF(HM10922) (KCCM-10511), BL21/poDLHF_B/S(HM10923) (KCCM-10512), BL21/pmsoDLHF_N/S(HM10924) (KCCM-10513) or BL21/pmsoDLHF_S/K(HM10925) (KCCM-10516).

As the antibody fragment expressed according to the inventive method is secreted into the periplasmic space of the host cell or into the culture medium, the antibody fragment can be harvested without going through steps such as osmotic shock treatment.

The target antibody fragment that can be expressed by the inventive method, preferably Fab, Fab', F(ab')$_2$ or scFv, is not limited to the antibody fragment of anti-tumor necrosis factor-α, and accordingly, the inventive method can be applied to the production of any antibody fragment used for diagnosis or treatment, for example, the antibody fragment having anti-cancer effect or the antibody fragment against several cytokines harmful to a human body when over-expressed.

As stated above, the recombinant expression vector of the present invention which comprises the *E. coli* thermostable enterotoxin signal sequence derivative or the *E. coli* outer membrane protein A signal sequence can express the antibody fragment in a soluble heterozygote form having antigen-binding affinity, and the microorganism transformed with the expression vector can secrete the antibody fragment into the periplasmic space of the host cell or into the culture medium, and therefore, the expressed antibody fragment can be easily harvested in a manner suitable for mass-production. Accordingly, it can be effectively used for the preparation of a diagnostic reagent or a therapeutic antibody.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

Example 1

Cloning of the Gene Encoding Anti-Tumor Necrosis Factor-α Fab'

Variable regions of a heavy chain and a light chain of human anti-tumor necrosis factor-α Fab' were synthesized using a nucleotide synthesizer, referring to the nucleotide sequences disclosed in International Patent No: WO97/29131. Gene fragments for cloning the light chain variable region had the nucleotide sequences of SEQ ID NOs: 1 to 6, and gene fragments for cloning the heavy chain variable region had the nucleotide sequences of SEQ ID NOs: 7 to 12. To facilitate the subsequent cloning procedure, recognition sites of HindIII and PvuI restriction enzymes were inserted into the first gene fragment of each of the genes encoding the light chain and the heavy chain (i.e., SEQ ID NOs: 1 and 7), respectively. Each of the synthesized gene fragments of the light chain and the heavy chain was mixed in one tube and subjected to a conventional PCR to link them in one gene sequence, respectively, to obtain the genes encoding the light chain and the heavy chain variable regions. In this PCR reaction, each of the gene fragments could act as a primer as well as a template, and accordingly, they annealed to each other to form a gene fragment having the size of about 320 mer. The PCR reaction mixture was prepared by mixing 100 pmole each of gene fragments, 5 μl of 2 mM dNTP mixture, 2.5 units of pfu DNA polmerase (Stratagen) and 5 μl of pfu reaction buffer (100 mM Tris-HCl [pH 8.3], 15 mM MgCl$_2$, 500 mM KCl) and adjusting its final volume to 50 μl with distilled water. The PCR was conducted under the condition of 30 cycles of 60 sec at 94° C., 60 sec at 60° C., and 60 sec at 72° C. after initial denaturation of 5 min at 94° C. using a DNA thermocycler (Perkin-Elmer).

In order to clone a gene encoding a light chain constant region and a gene encoding a heavy chain constant region comprising IgG1 CH1 and a hinge region of human anti-tumor necrosis factor-α Fab', RNA was extracted from human blood corpuscle cells and subjected to RT-PCR. A total RNA was extracted from about 6 Me of blood using a Qiamp RNA blood kit (Qiagen) and used as a template in RT-PCR. Each of the genes encoding the heavy chain and the light chain constant regions was amplified with a One-Step RT-PCR kit (Qiagen) using the primer pair of SEQ ID NOs: 13 and 14 for the heavy chain amplification, and the primer pair of SEQ ID NOs: 15 and 16 for the light chain amplification. At this time, to facilitate the subsequent cloning procedure, recognition sites of HindIII and StuI restriction enzymes were inserted into the heavy chain 5'-primer of SEQ ID NO: 26; a recognition site of BamHI restriction enzyme including a termination codon, into the heavy chain 3'-primer of SEQ ID NO: 27; recognition sites of HindIII and NruI restriction enzymes, into the light chain 5'-primer of SEQ ID NO: 28; and a recognition site of BamHI restriction enzyme including a termination codon, into the light chain 3'-primer of SEQ ID NO: 29. The PCR products encoding the heavy chain and the light chain constant regions were digested with HindIII and BamHI, respectively, and inserted into plasmid pBluscript SK(−) (Stratagen) pre-treated with the same enzymes, to prepare plasmids pBH and pBL (FIG. 1). It was found by DNA sequencing analysis that the constant regions of the heavy chain and the light chain were accurately inserted into the plasmid pBH and pBL, respectively.

Figure 2:
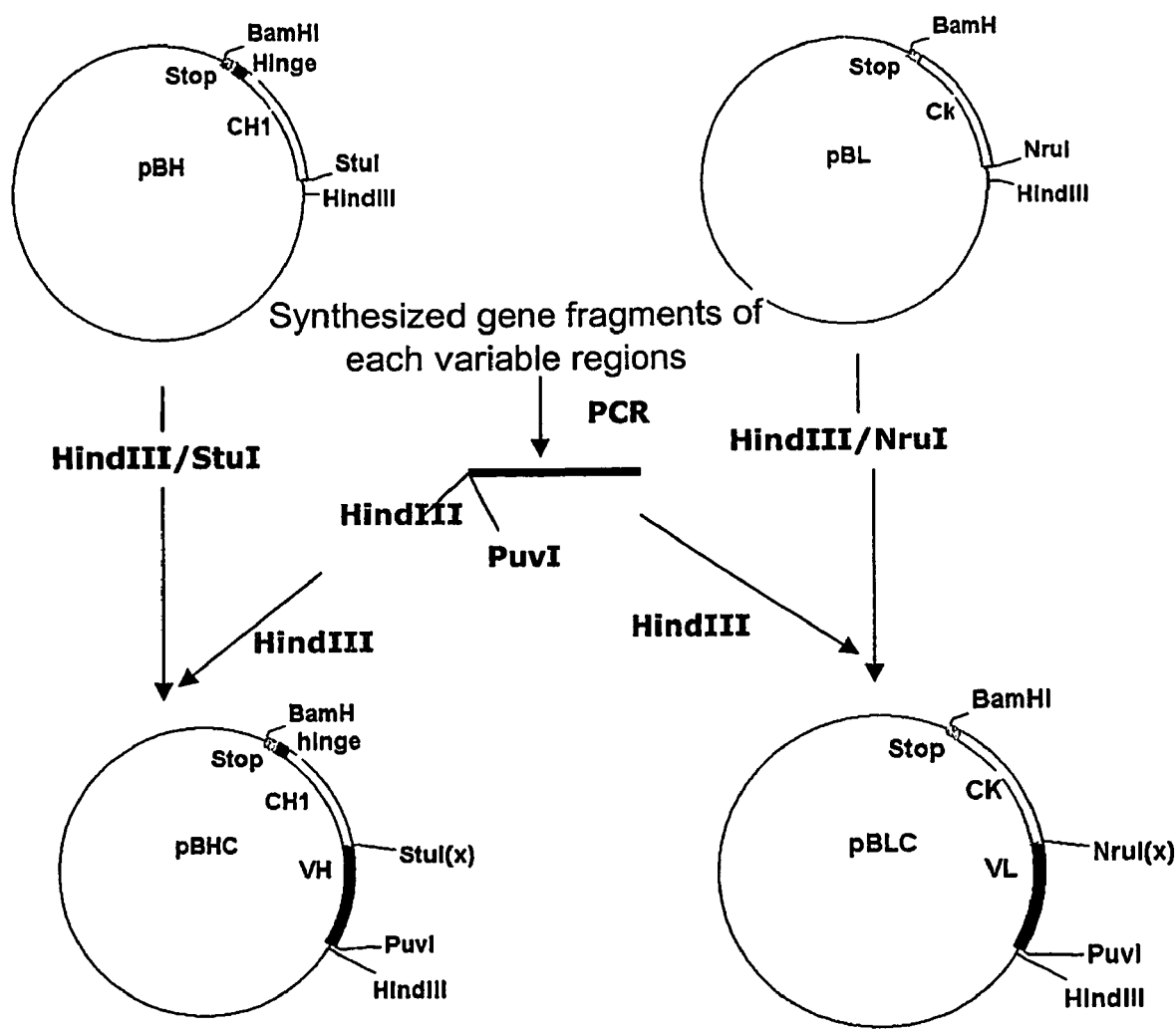
FIG. 2: the procedures of constructing plasmids pBHC and pBLC by inserting variable regions of the heavy chain and the light chain into plasmids pBH and pBL, respectively.

To link the variable regions of the heavy chain and the light chain with the corresponding constant regions, each variable region of the heavy chain and the light chain thus synthesized by PCR was digested with HindIII. The enzyme treated heavy chain variable region was inserted into plasmid pBH pre-treated with HindIII/StuI, and the enzyme treated light chain variable region was inserted into plasmid pBL pre-treated with HindIII/NruI, to construct plasmids pBHC and pBLC, respectively, in which each of the variable regions of the heavy chain and the light chain was linked to the corresponding constant regions (FIG. 2). The heavy chain and the light chain inserted into the plasmids pBHC and pBLC had the nucleotide sequences of SEQ ID NOs: 32 and 33, respectively.

Example 2

Construction of Anti-Tumor Necrosis Factor-α Fab' Gene Expression Vector

<2-1> Construction of an Expression Vector Comprising *E. coli* Thermostable Enterotoxin Signal Sequence Derivative and Anti-Tumor Necrosis Factor-α Fab'

To construct an expression vector using *E. coli* thermostable enterotoxin signal sequence derivative, expression vector pT14S1SH-4T20V22Q (Korean Patent No: 316347) expressing human growth hormone (hGH) was employed. The expression vector contained a thermostable enterotoxin signal sequence derivative having the nucleotide sequence of SEQ ID NO: 17. In order to remove the hGH gene from the expression vector and insert the gene fragment encoding the heavy chain and the light chain prepared in Example 1 into the same site, a recognition site of StuI restriction enzyme was inserted into the fusion site between the thermostable enterotoxin signal sequence derivative and the hGH gene of plasmid pT14S1SH-4T20V22Q by site-directed mutagenesis using a primer pair of SEQ ID NOs: 18 and 19. It was found from the result of sequencing analysis that the StuI recognition site was successfully generated at the target site. The plasmid having the StuI recognition site within plasmid pT14S1SH-4T20V22Q was designated pmSTII.

Figure 3:
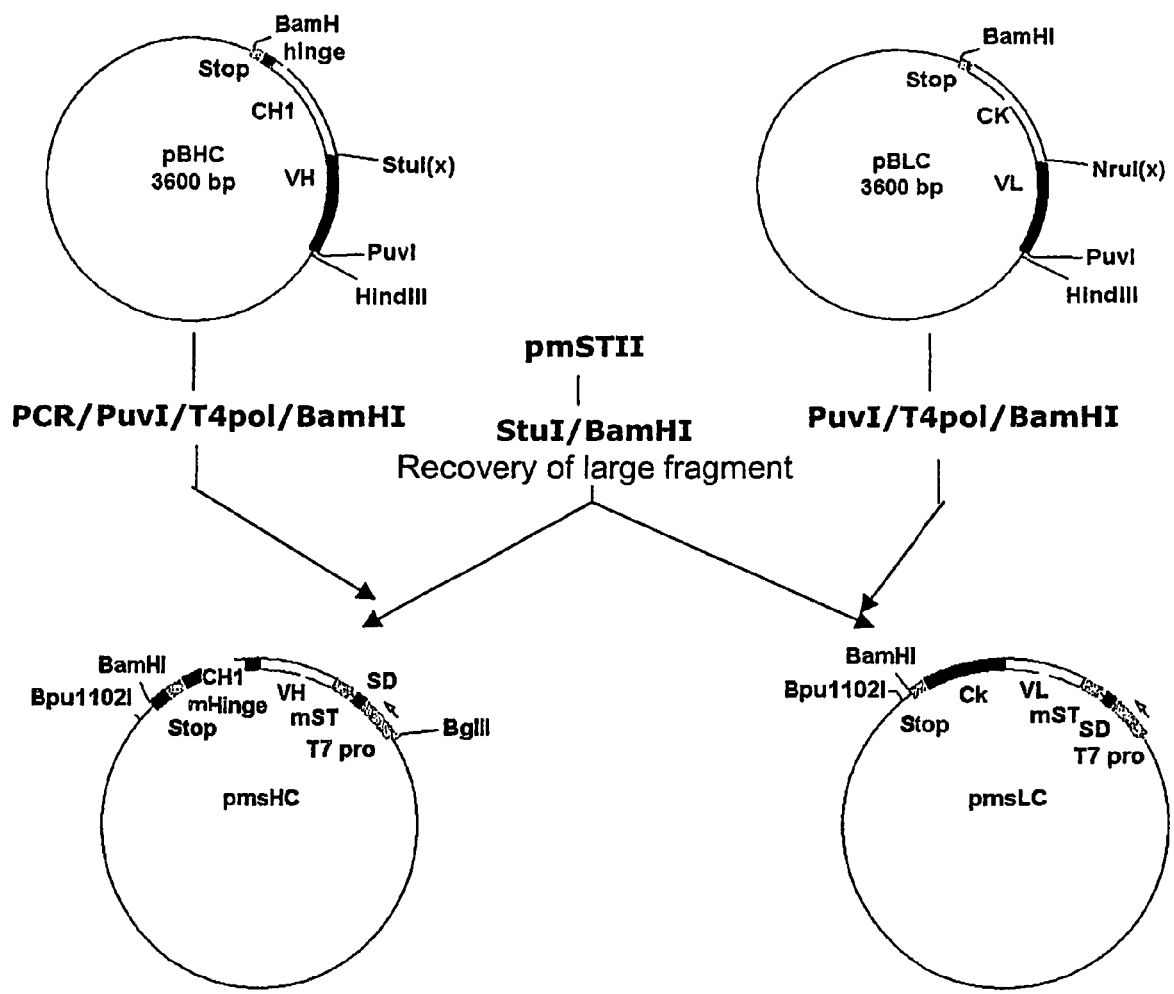
FIG. 3: the procedures of constructing expression vector pmsLC comprising T7 promoter and a gene encoding the light chain of the antibody fused with *E. coli* thermostable enterotoxin signal sequence, and expression vector pmsHC comprising T7 promoter and a gene encoding the heavy chain of the antibody fused with *E. coli* thermostable enterotoxin signal sequence, respectively.

After plasmid pmSTII was treated with StuI/BamHI and subjected to agarose gel electrophoresis, a large fragment (4.7 kb) containing the *E. coli* thermostable enterotoxin signal sequence derivative with the removal of hGH was excised from the gel. After plasmid pBLC having the gene fragment encoding the light chain prepared in Example 1 was treated with PuvI, its both ends were treated with T4 DNA polymerase to make blunt ends. The resulting plasmid was treated with BamHI and the gene fragment encoding the light chain having the size of about 720 bp was recovered. Further, PCR was carried out using the plasmid pBHC containing the gene fragment encoding the heavy chain as a template and a primer pair of SEQ ID NOs: 1 and 20. The PCR product thus amplified was treated with the same enzymes as those used in the preparation of the gene fragment encoding the light chain, to recover the gene fragment encoding the heavy chain having the size of about 700 bp. Since the primer of SEQ ID NO: 20 was designed to insert the amino acid sequence of EPKSCD-KTHTCAA-termination codon, the modified hinge sequence comprising a part of the heavy chain hinge region, into the gene fragment encoding the heavy chain, and contained a recognition site of BamHI restriction enzyme, it could be effectively used for the construction of Fab' expression vector in the following procedure. Each of the genes fragment encoding the heavy chain and the light chain thus prepared was inserted into the plasmid pmSTII fragment, to construct plasmid pmsHC comprising the gene fragment encoding the heavy chain fused with the thermostable enterotoxin signal sequence derivative as well as plasmid pmsLC comprising the gene fragment encoding the light chain fused with the thermostable enterotoxin signal sequence derivative (FIG. 3).

In order to construct a di-cistronic expression vector such that the heavy chain and the light chain can be expressed and secreted under the control of a single promoter, PCR was carried out using plasmid pmsHC comprising the gene fragment encoding the heavy chain fused with the thermostable enterotoxin signal sequence derivative as a template and two primer pairs of SEQ ID NOs: 21 and 20 and SEQ ID NOs: 22 and 23. The 5'-primer of SEQ ID NO: 21 was designed to initiate PCR from Shine-Dalgarno (SD) sequence necessary for the expression of the gene fragment encoding the heavy chain, and also contained a BamHI recognition site for easy cloning of the amplified product. In addition, the primer pair of SEQ ID NOs: 22 and 23 had the same nucleotide sequences of the primer pair of SEQ ID NOs: 21 and 20 except that they contained a recognition site of BpuI restriction enzyme, not the BamHI recognition site, to change the cloning site. The gene fragments encoding the heavy chain amplified with each primer pairs (one comprised the BamHI recognition site, and the other comprised the BpuI recognition site) were treated with BamHI and BpuI, respectively.

Figure 4:
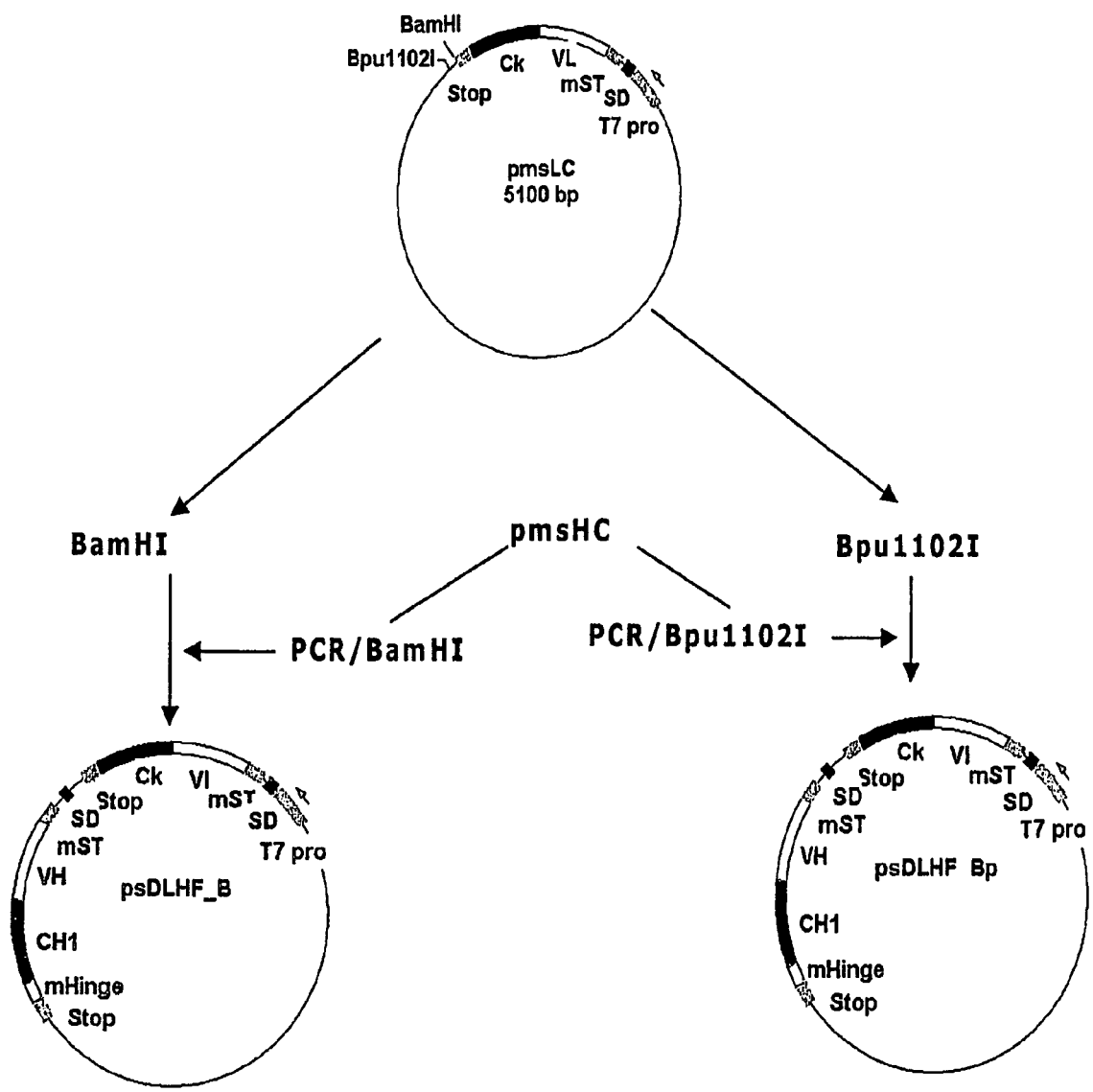
FIG. 4: the procedures of constructing di-cistronic expression vectors psDLHF_B and psDLHF_Bp that respectively express and secrete the heavy chain and the light chain under the control of a single T7 promoter.

The recognition sites of BamHI and BpuI in plasmid pmsLC comprising the gene fragment encoding the light chain fused with the thermostable enterotoxin signal sequence derivative were located downstream from the termination codon of the light chain, the BpuI recognition site being located further downstream by about 60 nucleotides than the BamHI recognition site. After plasmid pmsLC was treated with BamHI and BpuI, the gene fragment encoding the heavy chain treated with BamHI or BpuI was inserted thereto. The Fab' expression vector comprising the heavy chain gene fragment inserted into the BamHI recognition site of plasmid pmsLC was designated psDLHF_B, and the Fab' expression vector comprising the gene fragment encoding the heavy chain inserted into the BpuI recognition site of plasmid pmsLC was designated psDLHF_Bp (FIG. 4). In these expression vectors, each the genes encoding the heavy chain and the light chain is fused with the *E. coli* thermostable enterotoxin signal sequence, and a single T7 promoter regulates the expression of the genes encoding the light chain and the heavy chain. *E. coli* BL21(DE3) was transformed with each of the expression vectors, to prepare *E. coli* transformants BL21 (DE3)/psDLHF_B(HM10920) and BL21 (DE3)/psDLHF_BP(HM10921), respectively, and the *E. coli* transformants were deposited at Korean Culture Center of Microorganism on Oct. 2, 2003 under the accession numbers of KCCM-10509 and KCCM-10510.

<2-2> Construction of an Expression Vector Comprising *E. coli* Outer Membrane Protein A (OmpA) Signal Sequence and Anti-Tumor Necrosis Factor-α Fab'

An expression vector secretively expressing the genes encoding the heavy chain and the light chain of anti-tumor necrosis factor-α using *E. coli* OmpA signal sequence (SEQ ID NO: 24) was constructed as follows.

Plasmid pFlag.CTS (Eastman Chemical Company) containing Tac promoter and OmpA signal sequence was treated with HindIII, and the plasmid's HindIII recognition site was treated with Klenow DNA polymerase (NEB, New Egland Biolab USA) to make a blunt end, which was treated with BglII to construct a vector fragment having 5'-blunt end and 3'-sticky end. Further, to link each the genes encoding the heavy chain and the light chain to the OmpA signal sequence, PCR was carried out using plasmid pBHC comprising the gene fragment encoding the heavy chain as a template and a primer pair of SEQ ID NOs: 25 and 26, to amplify the PCR product comprising the variable region and the constant region of the heavy chain, a modified hinge region and a termination codon. At this time, the primer of SEQ ID NO: 26 corresponding to the 3'-end was designed to include an inserted recognition site of BglII restriction enzyme. The amplified gene fragment encoding the heavy chain was treated with BglII, and the resulting fragment was inserted into plasmid pFlag.CTS pre-treated with BglII, to construct plasmid poHC comprising the gene fragment encoding the heavy chain fused with the OmpA signal sequence. According to the same method as described above, PCR was carried out using plasmid pBLC comprising the gene fragment encoding the light chain as a template and a primer pair of SEQ ID NOs: 27 and 28, the PCR product thus amplified was subjected to the same enzyme treatment and inserted into plasmid pFlag.CTS, to construct plasmid poLC comprising the gene fragment encoding the light chain fused with the OmpA signal sequence.

In order to construct a di-cistronic expression vector such that each of the genes encoding the heavy chain and the light chain fused with the respective OmpA signal sequences can be expressed and secreted under the control of a single Tac promoter, PCR was carried out using plasmid poHC as a template and a primer pair of SEQ ID NOs: 29 and 30. The PCR product thus amplified had the SalI recognition site at both ends, Shine-Dalgano sequence necessary for the expression of the heavy chain except a promoter region and OmpA signal sequence. After the PCR product was treated with SalI, the recovered gene fragment was inserted into plasmid poLC pre-treated with the same enzyme, to construct expression vector poDLHF expressing the Fab' gene (FIG. 5). *E. coli* BL21 was transformed with the expression vector poDLHF to prepare *E. coli* transformant BL21/poDLHF(HM10922) and the *E. coli* transformant was deposited at Korean Culture Center of Microorganism on Oct. 2, 2003 under the accession number of KCCM-10511.

<2-3> Construction of an Expression Vector Regulated by a Dual-Promoter System

An expression vector having a dual-promoter system that can express and secrete the heavy chain and the light chain of anti-tumor necrosis factor-α Fab' under the control of independent promoters, respectively, was constructed as follows. Plasmid poHC of Example <2-2> comprising the gene fragment encoding the heavy chain of anti-tumor necrosis factor-α Fab' fused with the OmpA signal sequence was treated with BamHI and SalI. The enzyme-treated plasmid was subjected to agarose gel electrophoresis, and a smaller fragment (1.2 kb) comprising the gene fragment encoding the heavy chain of anti-tumor necrosis factor-α Fab', Tac promoter and OmpA signal sequence was excised from the gel. Both ends of the fragment were treated with a Klenow DNA polymerase to make blunt ends. Further, plasmid poLC of Example <2-2> comprising the gene fragment encoding the light chain of anti-tumor necrosis factor-α Fab' was treated with SalI, and then, both ends were also made blunt by the same method. The gene fragment encoding the heavy chain was then inserted thereto, to construct expression vector poDLHF_B/S which expressed and secreted each of the genes encoding the heavy chain and the light chain fused with the OmpA signal sequence independently under the control of Tac promoter (FIG. 6). *E. coli* BL21 was transformed with the expression vector poDLHF_B/S to prepare *E. coli* transformant BL21/poDLHF_B/S(HM10923), and the *E. coli* transformant was deposited at Korean Culture Center of Microorganism on Oct. 2, 2003 under the accession number of KCCM-10512.

<2-4> Construction of an Expression Vector which Regulates the Expression and Secretion of Each Chains by Different Signal Sequences

<2-4-1>

An expression vector having the gene encoding the light chain of anti-tumor necrosis factor-α Fab' fused with the thermostable enterotoxin signal sequence derivative and the gene encoding the heavy chain fused with the OmpA signal sequence, the expression and secretion thereof being regulated by a single promoter, was constructed as follows.

After expression vector poDLHF of Example <2-2> which expressed each of the genes encoding the heavy chain and the light chain fused with the OmpA signal sequence under the control of a single Tac promoter was treated with NdeI and SacI, the resulting vector was subjected to agarose gel electrophoresis, and a larger fragment (6.6 kb) was excised from the gel. The NdeI recognition site was located at the first amino acid, methionine of the OmpA signal sequence, and the SacI recognition site was located at the constant region of the light chain. Accordingly, when the expression vector was treated with NdeI and SacI, a gene fragment having no OmpA signal sequence, but the whole variable region of the light chain and a part of the constant region of the light chain was obtained.

PCR was carried out using the plasmid pmsLC comprising the gene fragment encoding the heavy chain fused with the thermostable enterotoxin signal sequence derivative as a template and a primer pair of SEQ ID NOs: 31 and 20. The 5'-primer of SEQ ID NO: 31 had NdeI recognition site bound to the first amino acid of thermostable enterotoxin signal sequence, and the 3'-primer of SEQ ID NO: 20 had SacI recognition site. The PCR product thus amplified was treated with NdeI and SacI, and was inserted into plasmid poDLHF having the deleted light chain region, to construct expression vector pmsoDLHF_N/S (FIG. 7). *E. coli* BL21 was transformed with the expression vector pmsoDLHF_N/S to prepare *E. coli* transformant BL21/pmsoDLHF_N/S (HM10924), and the *E. coli* transformant was deposited at Korean Culture Center of Microorganism on Oct. 2, 2003 under the accession number of KCCM-10513.

<2-4-2>

Unlike the expression vector prepared in Example <2-4-1>, an expression vector having the gene encoding the heavy chain of anti-tumor necrosis factor-α Fab' is fused with the thermostable enterotoxin signal sequence derivative and the gene fragment encoding the light chain is fused with the OmpA signal sequence, the expression and secretion thereof being regulated by a single promoter, was constructed as follows.

After expression vector psDLHF_Bp of Example <2-1> was treated with SacI and KpnI and subjected to agarose gel electrophoresis, a smaller fragment (0.6 kb) was excised from the gel. The SacI recognition site was located at the constant region of the light chain and the KpnI recognition site was located at the constant region of the heavy chain, and accordingly, the recovered fragment comprised the gene fragment encoding the light chain fused with the thermostable enterotoxin signal sequence derivative. Expression vector poDLHF which expresses each of the genes encoding the heavy chain and the light chain fused with the OmpA signal sequence regulated by a single Tac promoter was treated with the same enzymes, SacI and KpnI, and subjected to agarose gel electrophoresis. Then, a large fragment (7.4 kb) was excised from the gel and linked to the gene encoding the light chain recovered above, to construct expression vector pmsoDLHF_S/K (FIG. 8). *E. coli* BL21 was transformed with the expression vector pmsoDLHF_S/K to prepare *E. coli* transformant BL21/pmsoDLHF_S/K(HM10925), and the *E. coli* transformant was deposited at Korean Culture Center of Microorganism on Oct. 2, 2003 under the accession number of KCCM-10516.

Example 3

Expression of Anti-Tumor Necrosis Factor-α Fab' Gene

*E. coli* transformants HM10920 to HM10925 prepared in Example 2 were inoculated into a fermentor (Marubishi) in volume of 5 l, subjected to fermentation, and then, the expression of the anti-tumor necrosis factor-α Fab' by each of the *E. coli* transformants was examined as follows.

Each of the *E. coli* transformants was cultured in 100 Ml of LB medium with shaking overnight, inoculated into the fermentor and subjected to main-culture. The fermentor's temperature was maintained at 35° C. or 30° C., air was injected into the fermentor at a rate of 20 vvm to prevent the development of an anaerobic condition, and the culture medium was stirred at 500 rpm. A supplementary energy source of glucose and a yeast extract with the growth of microorganism was supplied considering the fermentation state of microorganism. When the OD value at 600 nm reached 80, IPTG, an inducer, was added to the fermentor. The fermentation was further carried out for 40 to 45 hours until the OD value at 600 nm became 120 to 140.

The fermented culture solution was subjected to centrifugation (20,000 g, 30 min) to obtain a supernatant, and the supernatant was subjected to ELISA to measure the amount of anti-tumor necrosis factor-α Fab' expressed from each transformant. After a monoclonal antibody (MAB1304, Chemicon international) against human antibody CH1 was dissolved in 10 mM carbonate buffer (pH 9.6) at a concentration of 1 μg/Ml, a 96-well plate was coated with the antibody solution at a concentration of 200 ng per well at 4° C. overnight and washed three times with PBS-T solution (137 mM NaCl, 2 mM KCl, 10 mM $Na_2HPO_4$, 2 mM $KH_2PO_4$, 0.05% Tween 20). A blocking buffer was prepared by dissolving bovine serum albumin in the PBS-T solution at a concentration of 1%. After 250 μl of the blocking solution was dropped to each well, the well plate was kept at room temperature for 1 hr and washed three times with the same PBS-T solution. Standard and sample solutions were diluted with the PBS-T solution at a proper concentration and added to the well coated with the antibody. The well plate was kept at room temperature for 1 hr for an antigen-antibody reaction and washed three times with the PBS-T solution. The standard solution was prepared by digesting human immunoglobulin-G (IB-globulin A, Green cross PBM) with a protease, papain, purifying the Fab using a series of columns, dissolving the Fab in the PBS-T solution at a concentration of 1 ng/Ml, and subjecting the standard solution to two-fold dilution. A conjugate sample (A7164, Sigma), a multiclonal antibody against the human light chain constant region covalently bound to a peroxidase, was used after diluting with the blocking buffer by 1000:1. 200 μl of the diluted sample was dropped to each well, and the well plate was kept at room temperature for 1 hr. After the reaction was completed, each well was washed three times with the PBS-T solution. Coloring solutions A and B (Color A—Stabilized peroxide solution and Color B—stabilized chromogen solution, DY 999, R&D Systems) were mixed in equal volume, 200 μl of the coloring solution mixture was added to each well, and then, the well plate was kept for 30 min. Then, 50 μl of 2 M sulfuric acid was added to each well to arrest the reaction. The well plate was analyzed with a microplate reader (Molecular Device) to measure the absorbance at 450 nm of the standard and sample solutions. The results are described in Table 1.

TABLE 1

| Transformant | Expression vector | Expression level (mg/, in a culture medium) |
| --- | --- | --- |
| HM10920 (KCCM-10509) | psDLHF_B | 80 |
| HM10921 (KCCM-10510) | psDLHF_Bp | 100 |
| HM10922 (KCCM-10511) | poDLHF | 250 |
| HM10923 (KCCM-10512) | poDLHF_B/S | 30 |
| HM10924 (KCCM-10513) | pmsoDLHF_N/S | 500 |
| HM10925 (KCCM-10516) | pmsoDLHF_S/K | 80 |

Example 4

Confirmation of the Protein Expression

<4-1> SDS-PAGE

In order to detect the anti-tumor necrosis factor-α Fab' expressed from each of the E. coli transformants prepared in Example 3, the expressed protein was partially purified by using a protein G column having high affinity to Fab and subjected to SDS-PAGE analysis as follows.

A Hitrap Protein G HP column (Amersharm Bioscience) was sufficiently equilibrated with 10 column volume of an equilibration buffer (20 mM sodium phosphate, pH 7.0) at a flow rate of 1 Ml per minute, and the fermented culture supernatant obtained in Example 3 was loaded onto the column. After the sample loading was completed, the column was washed with 10 column volume of the equilibration buffer, and the anti-tumor necrosis factor-α Fab' absorbed to the column was eluted from the column with 5 column volume of an eluting solution (0.1 M glycine-HCl, pH 2.7).

Figure 9:
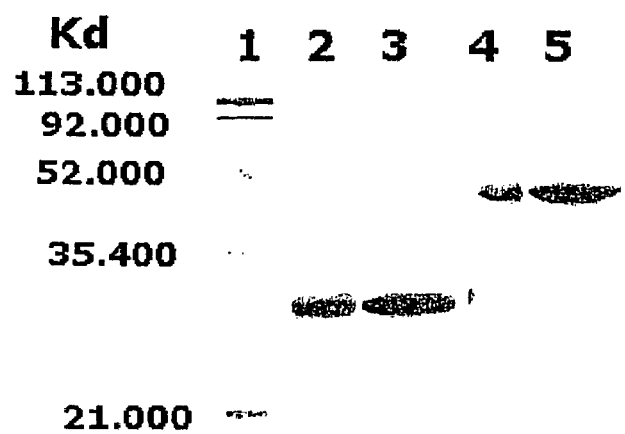
FIG. 9: the result of comparing the expression patterns of anti-tumor necrosis factor-α Fab' expressed from the *E. coli* transformant with SDS-PAGE analyses conducted under reducing and non-reducing conditions.

Since the anti-tumor necrosis factor-α Fab' thus eluted was a heterozygote formed by binding two different proteins, i.e., the heavy and the light chain linked by a disulfide bond, its migration patterns between reducing and non-reducing SDS-PAGE analyses become different. FIG. 9 shows the result of comparing the migration patterns of the purified anti-tumor necrosis factor-α Fab' in reducing and non-reducing SDS-PAGE analyses using 15% criterion gel (Bio-Rad). In FIG. 9, lanes 2 and 3 were the results of reducing SDS-PAGE and lanes 4 and 5 were the results of non-reducing SDS-PAGE. Lane 1 was a pre-stained low-range standard marker (Bio-Rad); lanes 2 and 4 were the Fab standard protein used in Example 3; and lane 3 and 5 were the purified sample produced by fermenting the E. coli transformant HM10922 (KCCM-10511).

As shown in FIG. 9, the binding between the heavy chain and the light chain in reducing SDS-PAGE was reductively cleaved, and accordingly, the heavy chain and the light chain migrated as separate monomers of approximately same size (since a molecular weight of the heavy chain (about 24 kDa) is similar to that of the light chain (about 23 kDa), they appeared as one molecule in the gel). On the other hand, the heavy chain and the light chain existed as a heterozygote, a linked form through a disulfide bond, in non-reducing SDS-PAGE, and accordingly, showed a migration distance of about 47 kDa.

<4-2> N-Terminal Sequencing Analysis

In order to analyze the amino acid sequence of the heterozygote having the molecular weight of about 47 kDa which was determined by SDS-PAGE in Example <4-1> at Korea Basic Science Institute (KBSI, Seoul branch), a sample was prepared as follows.

A PVDF membrane (Bio Rad) was activated by soaking in methanol for about 2 to 3 sec, and the activated membrane was sufficiently wetted with a blocking solution (170 mM glycine, 25 mM Tris-HCl [pH 8], 20% methanol). The non-reducing SDS-PAGE gel of Example <4-1> was subjected to blotting to the activated PVDF membrane using a blotting kit (Hoefer Semi-Dry Transfer unit, Amersham) for 1 hr. The protein transferred to the PVDF membrane was stained with Comassie Blue R-250 (Amnesco) for 3 to 4 sec, and washed with a destaining solution (water:acetic acid:methanol=5:1:4). The region containing the protein was excised from the washed membrane with a pair of scissors and used for N-terminal sequencing analysis.

The amino acid sequence of the light chain of anti-tumor necrosis factor-α Fab' was Asp-Ile-Gln-Met-Thr-Gln-Ser (SEQ ID NO: 34) and that of the heavy chain was Glu-Val-Gln-Leu-Glu-Val-Asp-Ser (SEQ ID NO: 35). As a result of amino acid sequencing analysis, it was found that the N-terminal amino acid sequences of the light and heavy chains of the heterozygote having the molecular weight of about 47 kDa secretively expressed from the inventive E. coli transformant corresponded to those of SEQ ID NOs: 34 and 35, respectively. These results confirmed that the heavy chain and the light chain of anti-tumor necrosis factor-α Fab' produced according to the present invention exists in the form of a normal heterozygote.

<4-3> Enzyme Linked Immunosorbent Assay (ELISA)

In order to examine whether the anti-tumor necrosis factor-α Fab' expressed from the E. coli transformant in Example 3 binds to a tumor necrosis factor-α antigen, enzyme linked immunosorbent assay (ELISA) was conducted as follows.

The concentration of anti-tumor necrosis factor-α Fab' obtained in Example <4-1> was measured by determining the absorption coefficient at 280 nm (extinction coefficient=1.43, Humphreys et, al. Protein Expression and Purification 26: 309-320, 2002), and then, dissolved in PBS-T buffer to a concentration of 10 ng/Ml. In addition, humira (Abbott) which has already been demonstrated to be a commercially effective arthritis therapeutic that binds to the tumor necrosis factor-α, was dissolved in the same buffer at the same concentration to be used as a standard antibody capable of binding to the tumor necrosis factor-α. A well plate was coated with the tumor necrosis factor-α according to the same method as described in Example 3, and examined was whether the standard antibody produced from animal cells and the Fab' produced from the inventive E. coli transformant show the same binding affinity at the same concentration. At this time, the standard antibody (control) was the Fab prepared by digesting human immunoglobulin-G with a protease, papain and purifying using a series of columns.

Figure 10:
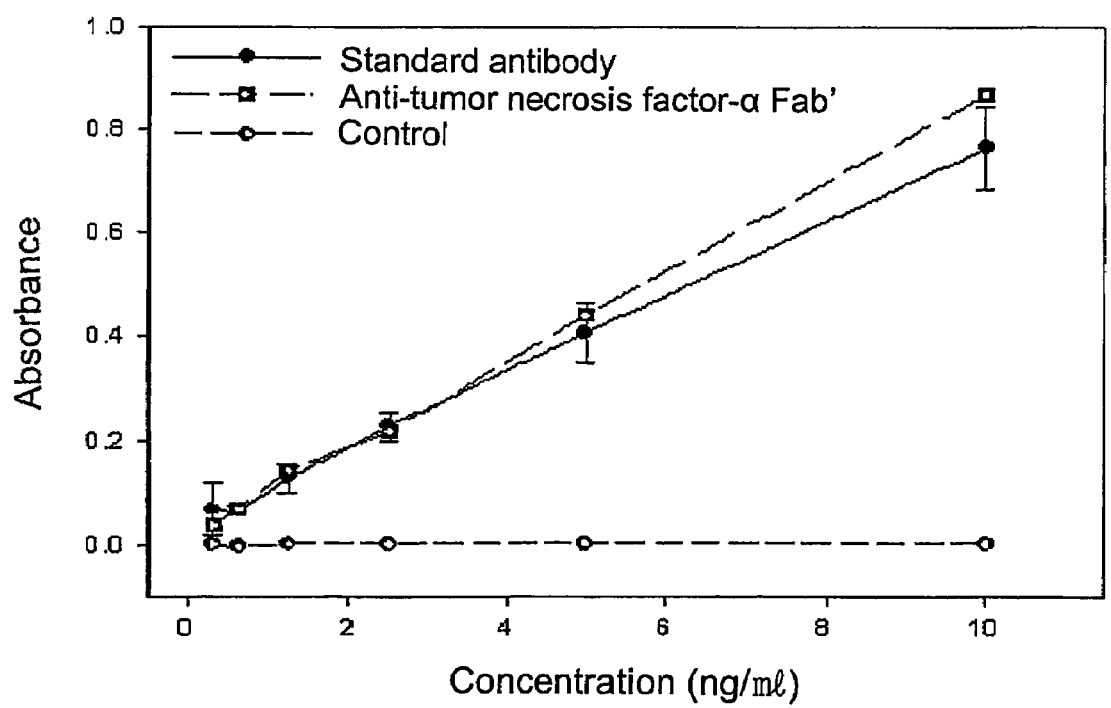
FIG. 10: the result of ELISA to examine whether the anti-tumor necrosis factor-α Fab' expressed from the *E. coli* transformant binds to tumor necrosis factor-α or not.

As shown in FIG. 10, while the Fab standard protein used as a control did not show any binding affinity to the tumor necrosis factor-α, the anti-tumor necrosis factor-α Fab' produced by the inventive E. coli transformant bound to the tumor necrosis factor-α in proportion to the dilution rate and showed the same or higher absorbance than the standard antibody.

While the embodiments of the subject invention have been described and illustrated, it is obvious that various changes and modifications can be made therein without departing from the spirit of the present invention which should be limited only by the scope of the appended claims.

What is claimed is:

1. A method for producing an antibody fragment, comprising the steps of:
   1) preparing an expression vector comprising a gene encoding a light chain of the antibody fragment fused with *E. coli* thermostable enterotoxin signal sequence derivative and a gene encoding a heavy chain of the antibody fragment fused with *E. coli* outer membrane protein A signal sequence, wherein the expression of the genes encoding the light chain and the heavy chain is regulated by a single promoter;
   2) transforming a microorganism with the expression vector;
   3) culturing the transformed microorganism in a medium; and
   4) collecting the antibody fragment from the medium or from the microorganism.

2. The method of claim 1, wherein the antibody fragment is derived from a chimeric antibody, a humanized antibody or a human antibody.

3. The method of claim 1, wherein the antibody fragment is selected from the group consisting of Fab, Fab', F(ab')$_2$ and scFv.

4. The method of claim 1, wherein the *E. coli* thermostable enterotoxin signal sequence derivative has the nucleotide sequence of SEQ ID NO: 17 and the *E. coli* outer membrane protein A signal sequence has the nucleotide sequence of SEQ ID NO: 23.

5. The method of claim 1, wherein the promoter is T7 promoter or Tac promoter.

6. The method of claim 1, wherein the antibody fragment is a fragment of anti-tumor necrosis factor-alpha antibody.

7. The method of claim 1, wherein the expression vector is pmsoDLHF_N/S.

8. The method of claim 1, wherein the microorganism is *E. coli*.

9. The method of claim 8, wherein the microorganism transformed with the expression vector is *E. coli* BL21/pmsoDLHF_N/S(HM10924) (KCCM-10513).

10. An expression vector comprising a gene encoding a light chain of the antibody fragment fused with *E. coli* thermostable enterotoxin signal sequence derivative and a gene encoding a heavy chain of the antibody fragment fused with *E. coli* outer membrane protein A signal sequence, wherein the expression of the genes encoding the light chain and the heavy chain is regulated by a single promoter, and the antibody fragment expressed from the expression vector is secreted into a culture medium where a host carrying the expression vector is cultured or into a periplasmic space of the host.

11. The expression vector of claim 10, wherein the antibody fragment is derived from a chimeric antibody, a humanized antibody or a human antibody.

12. The expression vector of claim 10, wherein the antibody fragment is selected from the group consisting of Fab, Fab', F(ab')$_2$ and scFv.

13. The expression vector of claim 10, wherein the *E. coli* thermostable enterotoxin signal sequence derivative has the nucleotide sequence of SEQ ID NO: 17 and the *E. coli* outer membrane protein A signal sequence has the nucleotide sequence of SEQ ID NO: 23.

14. The expression vector of claim 10, wherein the antibody fragment is a fragment of anti-tumor necrosis factor-alpha antibody.

15. The expression vector of claim 10, wherein the promoter is T7 promoter or Tac promoter.

16. The expression vector of claim 15, which is pmsoDLHF_N/S.

17. A microorganism transformed with the expression vector of claim 10.

18. The microorganism of claim 17, which is *E. coli*.

19. The microorganism of claim 18, which is *E. coli* BL21/pmsoDLHF_N/S(HM10924) (KCCM-10513).

* * * * *

SEQUENCE LISTING

<160> NUMBER OF SEQ ID NOS: 35

<210> SEQ ID NO 1
<211> LENGTH: 75
<212> TYPE: DNA
<213> ORGANISM: Artificial Sequence
<220> FEATURE:
<223> OTHER INFORMATION: Synthetic construct

<400> SEQUENCE: 1
gggaagcttc gatcggacat ccagatgacc cagtctccat cctccctgtc tgcatctgta    60
ggggacagag tcacc                                                     75

<210> SEQ ID NO 2
<211> LENGTH: 80
<212> TYPE: DNA
<213> ORGANISM: Artificial Sequence
<220> FEATURE:
<223> OTHER INFORMATION: Synthetic construct

<400> SEQUENCE: 2 tggttttttgc tgataccagg ctaagtaatt tctgatgccc tgacttgccc gacaagtgat    60
ggtgactctg tcccctacag                                                80

<210> SEQ ID NO 3
<211> LENGTH: 80
<212> TYPE: DNA
<213> ORGANISM: Artificial Sequence
<220> FEATURE:
<223> OTHER INFORMATION: Synthetic construct

<400> SEQUENCE: 3
cctggtatca gcaaaaacca gggaaagccc ctaagctcct gatctatgct gcatccactt    60
tgcaatcagg ggtcccatct                                                80

<210> SEQ ID NO 4
<211> LENGTH: 80
<212> TYPE: DNA
<213> ORGANISM: Artificial Sequence
<220> FEATURE:
<223> OTHER INFORMATION: Synthetic construct

<400> SEQUENCE: 4
aggctgtagg ctgctgatgg tgagagtgaa atctgtccca gatccactgc cactgaaccg    60
agatgggacc cctgattgca                                                80

<210> SEQ ID NO 5
<211> LENGTH: 80

```
<212> TYPE: DNA
<213> ORGANISM: Artificial Sequence
<220> FEATURE:
<223> OTHER INFORMATION: Synthetic construct

<400> SEQUENCE: 5
ccatcagcag cctacagcct gaagatgttg caacttatta ctgtcaaagg tataaccgtg      60
caccgtatac ttttggccag                                                  80

<210> SEQ ID NO 6
<211> LENGTH: 41
<212> TYPE: DNA
<213> ORGANISM: Artificial Sequence
<220> FEATURE:
<223> OTHER INFORMATION: Synthetic construct

<400> SEQUENCE: 6
tttgatttcc accttggtcc cctggccaaa agtatacggt g                          41

<210> SEQ ID NO 7
<211> LENGTH: 75
<212> TYPE: DNA
<213> ORGANISM: Artificial Sequence
<220> FEATURE:
<223> OTHER INFORMATION: Synthetic construct

<400> SEQUENCE: 7
gggaagcttc gatcggaggt gcagctggtg gagtctgggg gaggcttggt acagcccggc      60
aggtccctga gactc                                                       75

<210> SEQ ID NO 8
<211> LENGTH: 79
<212> TYPE: DNA
<213> ORGANISM: Artificial Sequence
<220> FEATURE:
<223> OTHER INFORMATION: Synthetic construct

<400> SEQUENCE: 8
agcttgccgg acccagtgca tggcataatc atcaaaggtg aatccagagg ccgcacagga      60
gagtctcagg gacctgccg                                                   79

<210> SEQ ID NO 9
<211> LENGTH: 80
<212> TYPE: DNA
<213> ORGANISM: Artificial Sequence
<220> FEATURE:
<223> OTHER INFORMATION: Synthetic construct

<400> SEQUENCE: 9
tgcactgggt ccggcaagct cagggaagg gcctggaatg ggtctcagct atcacttgga       60
atagtggtca catagactat                                                  80

<210> SEQ ID NO 10
<211> LENGTH: 80
<212> TYPE: DNA
<213> ORGANISM: Artificial Sequence
<220> FEATURE:
<223> OTHER INFORMATION: Synthetic construct

<400> SEQUENCE: 10
atacagggag ttcttggcgt tgtctctgga gatggtgaat cggccctcca cagagtccgc      60
atagtctatg tgaccactat                                                  80
```

```
<210> SEQ ID NO 11
<211> LENGTH: 80
<212> TYPE: DNA
<213> ORGANISM: Artificial Sequence
<220> FEATURE:
<223> OTHER INFORMATION: Synthetic construct

<400> SEQUENCE: 11
acgccaagaa ctccctgtat ctgcaaatga acagtctgag agctgaggat acggccgtat      60
attactgtgc gaaagtctcg                                                  80

<210> SEQ ID NO 12
<211> LENGTH: 84
<212> TYPE: DNA
<213> ORGANISM: Artificial Sequence
<220> FEATURE:
<223> OTHER INFORMATION: Synthetic construct

<400> SEQUENCE: 12
cactcgagac ggtgaccagg gtaccttggc cccaatagtc aagggaggac gcggtgctaa      60
ggtacgagac tttcgcacag taat                                             84

<210> SEQ ID NO 13
<211> LENGTH: 39
<212> TYPE: DNA
<213> ORGANISM: Artificial Sequence
<220> FEATURE:
<223> OTHER INFORMATION: Synthetic construct

<400> SEQUENCE: 13
cccaagctta ggcctccacc aagggcccat cggtcttcc                             39

<210> SEQ ID NO 14
<211> LENGTH: 48
<212> TYPE: DNA
<213> ORGANISM: Artificial Sequence
<220> FEATURE:
<223> OTHER INFORMATION: Synthetic construct

<400> SEQUENCE: 14
gggggatcct tatgggcacg gtgggcatgt gtgagttttg tcacaaga                   48

<210> SEQ ID NO 15
<211> LENGTH: 42
<212> TYPE: DNA
<213> ORGANISM: Artificial Sequence
<220> FEATURE:
<223> OTHER INFORMATION: Synthetic construct

<400> SEQUENCE: 15
cccaagcttt cgcgaactgt ggctgcacca tctgtcttca tc                         42

<210> SEQ ID NO 16
<211> LENGTH: 42
<212> TYPE: DNA
<213> ORGANISM: Artificial Sequence
<220> FEATURE:
<223> OTHER INFORMATION: Synthetic construct

<400> SEQUENCE: 16
cccggatccc taacactctc ccctgttgaa gctctttgtg ac                         42

<210> SEQ ID NO 17
<211> LENGTH: 69
```

```
<212> TYPE: DNA
<213> ORGANISM: Artifical Sequence
<220> FEATURE:
<223> OTHER INFORMATION: Synthetic construct

<400> SEQUENCE: 17
atgaaaaaga caatcgcatt tcttcttgca tctatgttcg tttttttctat tgctacaaat      60 gcccaggcg                                                                69

<210> SEQ ID NO 18
<211> LENGTH: 45
<212> TYPE: DNA
<213> ORGANISM: Artificial Sequence
<220> FEATURE:
<223> OTHER INFORMATION: Synthetic construct

<400> SEQUENCE: 18
tctattgcta caaatgccca ggccttccca accattccct tatcc                        45

<210> SEQ ID NO 19
<211> LENGTH: 45
<212> TYPE: DNA
<213> ORGANISM: Artificial Sequence
<220> FEATURE:
<223> OTHER INFORMATION: Synthetic construct

<400> SEQUENCE: 19
agataacgat gtttacgggt ccggaagggt tggtaaggga atagg                        45

<210> SEQ ID NO 20
<211> LENGTH: 51
<212> TYPE: DNA
<213> ORGANISM: Artificial Sequence
<220> FEATURE:
<223> OTHER INFORMATION: Synthetic construct

<400> SEQUENCE: 20
gggggatcct cacgcggcgc atgtgtgagt tttgtcacaa gatttaggct c                 51

<210> SEQ ID NO 21
<211> LENGTH: 43
<212> TYPE: DNA
<213> ORGANISM: Artificial Sequence
<220> FEATURE:
<223> OTHER INFORMATION: Synthetic construct

<400> SEQUENCE: 21 ggggatcca ggaggtgatt tatgaaaaag acaatcgcat ttc                           43

<210> SEQ ID NO 22
<211> LENGTH: 44
<212> TYPE: DNA
<213> ORGANISM: Artificial Sequence
<220> FEATURE:
<223> OTHER INFORMATION: Synthetic construct

<400> SEQUENCE: 22
ggggctgagc aggaggtgat ttatgaaaaa gacaatcgca tttc                         44

<210> SEQ ID NO 23
<211> LENGTH: 52
<212> TYPE: DNA
<213> ORGANISM: Artificial Sequence
<220> FEATURE:
<223> OTHER INFORMATION: Synthetic construct
```

```
<400> SEQUENCE: 23
ggggctcagc tcacgcggcg catgtgtgag ttttgtcaca agatttaggc tc            52

<210> SEQ ID NO 24
<211> LENGTH: 63
<212> TYPE: DNA
<213> ORGANISM: E. coli

<400> SEQUENCE: 24 atgaaaaga cagctatcgc gattgcagtg gcactggctg gtttcgctac cgttgcgcaa     60
gct                                                                  63

<210> SEQ ID NO 25
<211> LENGTH: 30
<212> TYPE: DNA
<213> ORGANISM: Artificial Sequence
<220> FEATURE:
<223> OTHER INFORMATION: Syntheti construct

<400> SEQUENCE: 25
gaggttcagc tagtcgagtc aggaggcggt                                     30

<210> SEQ ID NO 26
<211> LENGTH: 51
<212> TYPE: DNA
<213> ORGANISM: Artificial Sequence
<220> FEATURE:
<223> OTHER INFORMATION: Synthetic construct

<400> SEQUENCE: 26
gggagatctt cacgcggcgc atgtgtgagt tttgtcacaa gatttaggct c              51

<210> SEQ ID NO 27
<211> LENGTH: 30
<212> TYPE: DNA
<213> ORGANISM: Artificial Sequence
<220> FEATURE:
<223> OTHER INFORMATION: Synthetic construct

<400> SEQUENCE: 27
gacattcaaa tgacccagag cccatccagc                                     30

<210> SEQ ID NO 28
<211> LENGTH: 42
<212> TYPE: DNA
<213> ORGANISM: Artificial Sequence
<220> FEATURE:
<223> OTHER INFORMATION: Synthetic construct

<400> SEQUENCE: 28
cccagatctc taacactctc ccctgttgaa gctctttgtg ac                       42

<210> SEQ ID NO 29
<211> LENGTH: 41
<212> TYPE: DNA
<213> ORGANISM: Artificial Sequence
<220> FEATURE:
<223> OTHER INFORMATION: Synthetic construct

<400> SEQUENCE: 29
ggggtcgaca ggaggtgatt tatgaaaaag acagctatcg c                        41

<210> SEQ ID NO 30
<211> LENGTH: 51
```

```
<212> TYPE: DNA
<213> ORGANISM: Artificial Sequence
<220> FEATURE:
<223> OTHER INFORMATION: Synthetic construct

<400> SEQUENCE: 30
ggggtcgact cacgcggcgc atgtgtgagt tttgtcacaa gatttaggct c         51

<210> SEQ ID NO 31
<211> LENGTH: 42
<212> TYPE: DNA
<213> ORGANISM: Artificial Sequence
<220> FEATURE:
<223> OTHER INFORMATION: Synthetic construct

<400> SEQUENCE: 31
gggcatatga aaagacaat cgcatttctt cttgcatcta tg                    42

<210> SEQ ID NO 32
<211> LENGTH: 705
<212> TYPE: DNA
<213> ORGANISM: Artificial Sequence
<220> FEATURE:
<223> OTHER INFORMATION: Synthetic construct

<400> SEQUENCE: 32
gaggttcagc tagtcgagtc aggaggcggt ttggtacagc ccggcaggtc cctgagactc    60
tcctgtgcgg cctctggatt caccttttgat gattatgcca tgcactgggt ccggcaagct  120
ccagggaagg gcctggaatg ggtctcagct atcacttgga atagtggtca catagactat   180
gcggactctg tggagggccg attcaccatc tccagagaca acgccaagaa ctccctgtat   240
ctgcaaatga acagtctgag agctgaggat acggccgtat attactgtgc gaaagtctcg   300
taccttagca ccgcgtcctc ccttgactat tggggccaag gtaccctggt caccgtctcg   360
agtgcctcca ccaagggccc atcggtcttc cccctggcac cctcctccaa gagcacctct   420 ggggcacag cggccctggg ctgcctggtc aaggactact ccccgaaacc ggtgacggtg    480
tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gaaagttgag   660
cccaaatctt gtgacaaaac tcacacatgc ccaccgtgcc catag                   705

<210> SEQ ID NO 33
<211> LENGTH: 645
<212> TYPE: DNA
<213> ORGANISM: Artificial Sequence
<220> FEATURE:
<223> OTHER INFORMATION: Synthetic construct

<400> SEQUENCE: 33
gacatccaga tgacccagtc tccatcctcc ctgtctgcat ctgtagggga cagagtcacc    60
atcacttgtc gggcaagtca gggcatcaga aattacttag cctggtatca gcaaaaacca   120
gggaaagccc ctaagctcct gatctatgct gcatccactt tgcaatcagg ggtcccatct   180
cggttcagtg gcagtggatc tgggacagat ttcactctca ccatcagcag cctacagcct   240
gaagatgttg caacttatta ctgtcaaagg tataaccgtg caccgtatac ttttggccag   300
gggaccaagg tggaaatcaa acgaactgtg gctgcaccat ctgtcttcat cttcccgcca   360
tctgatgagc agttgaaatc tggaactgcc tctgttgtgt gcctgctgaa taacttctat   420
```

-continued

```
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 34
<211> LENGTH: 7
<212> TYPE: PRT
<213> ORGANISM: Artificial Sequence
<220> FEATURE:
<223> OTHER INFORMATION: Synthetic construct

<400> SEQUENCE: 34

Asp Ile Gln Met Thr Gln Ser
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic construct

<400> SEQUENCE: 35

Glu Val Gln Leu Glu Val Asp Ser
1               5